(12) United States Patent
Cheung

(10) Patent No.: US 9,157,128 B2
(45) Date of Patent: Oct. 13, 2015

(54) KIT FOR DETECTING HIV-2 AND METHOD FOR DETECTING HIV-2 USING THE SAME

(75) Inventor: Win Den Cheung, Olney, MD (US)

(73) Assignee: Hanwha Techwin Co., Ltd., Changwon-Si (KR)

( * ) Notice: Subject to any disclaimer, the term of this patent is extended or adjusted under 35 U.S.C. 154(b) by 1100 days.

(21) Appl. No.: 13/160,054

(22) Filed: Jun. 14, 2011

(65) Prior Publication Data

US 2012/0045750 A1      Feb. 23, 2012

Related U.S. Application Data

(60) Provisional application No. 61/375,964, filed on Aug. 23, 2010.

(51) Int. Cl.
| | | |
|---|---|---|
| *C07H 21/04* | (2006.01) | |
| *C12Q 1/70* | (2006.01) | |
| *C12Q 1/68* | (2006.01) | |

(52) U.S. Cl.
CPC ............ *C12Q 1/703* (2013.01); *C12Q 2600/16* (2013.01)

(58) Field of Classification Search
None
See application file for complete search history.

(56) References Cited

U.S. PATENT DOCUMENTS

2002/0177131 A1* 11/2002 Fodor et al. .................. 435/6

OTHER PUBLICATIONS

"Cy2, Cy3, Cy5 1D gel imaging using Cy dye lighting unit and epi RGB LED module" [online] May 2010 [retrieved on Jan. 25, 2015] retrieved from: http://www.syngene.com/assets/doc/Technical-notes/Cy-dye-gel-imaging-47.pdf.*
"Applied Biosystems Standard Dye Sets for Genotyping Applications" [online] Oct. 2005 [retrieved on Jan. 25, 2015] retrieved from: http://faculty.georgetown.edu/hamiltm1/DNA_Fragment_Sizing_Facility_files/ABI%20Dye%Set%20card.pdf.*
"User manual: 4-Color Compensation Set for Check-Direct CPE" [online] Sep. 20, 2013 [retrieved on Jan. 25, 2015] retrieved from: http://check-points.com/downloads/manuals/4-Color_Compensation_Set_LC480_IFU_070-03_EN_20Sept2013.*
"Streptavidin-RED670™ Conjugate" [online] Sep. 13, 2001 [retrieved on Jan. 25, 2015] retrieved from: http://tools.lifetechnologies.com/content/sfs/manuals/19543024.pdf.*
"Lightning-Link® Rapid Texas Red® Conjugation Kit Data Sheet" [online] Jun. 24, 2014 [retrieved on Jan. 25, 2015] retrieved from: http://www.innovabiosciences.com/images/stories/innova/LL-Rapid%20Texas%20Red%20date%20sheet%20v1.pdf.*
"Real-Time PCR Systems Applied Biosystems 7900HT Fast Real-Time PCR System and 7300/7500 Real-Time PCR Systems Chemistry Guide" [online] May 2005 [retrieved on Jan. 25, 2015] retrieved from: http://www3.appliedbiosystems.com/cms/groups/mcb_marketing/documents/generaldocuments/cms_041440.pdf.*
"TYE™ 563" [online] [retrieved on Jan. 25, 2015] retrieved from: https://www.exiqon.com/ls/homeofIna/Chemistry/TYE%20563.pdf.*
"Biosearch Technologies Dye Selection, Handling, and Storage of BHQ Probes" [online] 2011 [retrieved on Jan. 25, 2015] retrieved from: http://www.biosearchtech.com/assets/bti_bhq_handling.pdf.*
"Iowa Black® Dark Quenchers" [online] [retrieved on Jan. 25, 2015] retrieved from: http://www.idtdna.com/site/Catalog/Modifications/Category/4.*

* cited by examiner

*Primary Examiner* — Samuel Woolwine
(74) *Attorney, Agent, or Firm* — Sughrue Mion, PLLC

(57) ABSTRACT

A kit for detecting HIV-2 strains in a test sample is disclosed. In addition a method is described for the real-time detection of HIV-2 strains in a test sample using the kit. According to method of detection, the results of the detection can be rapidly identified with a reduced number of copies of a sample in real-time.

11 Claims, 3 Drawing Sheets

KIT FOR DETECTING HIV-2 AND METHOD FOR DETECTING HIV-2 USING THE SAME

CROSS-REFERENCE TO RELATED APPLICATIONS

This application claims priority from U.S. Provisional Patent Application No. 61/375,964 filed on Aug. 23, 2010, the content of which is hereby incorporated by reference in its entirety.

FIELD

The disclosure describes a kit for detecting HIV-2 strains and a method of detecting HIV-2 strains by using the kit. Oligonucleotides suitable for use in the method are also disclosed.

BACKGROUND

Although not as recognized as human immunodeficiency virus type-1 (HIV-1), human immunodeficiency virus type-2 (HIV-2) also causes acquired immunodeficiency syndrome (AIDS) from the same infection route as HIV-1. Compared to HIV-1, HIV-2 more slowly weakens the human immune system. Moreover, AIDS caused by HIV-2 is less contagious at an early stage, but is more highly contagious at an advanced stage than AIDS caused by HIV-1.

A viral load test of HIV-2 has not been approved by the Food and Drug Administration (FDA). Since HIV, a pathogen that causes AIDS, was first isolated in the early 1980s, diverse research has been conducted into treating AIDS around the world. However, researchers have not succeeded in developing an effective vaccine capable of preventing and treating AIDS.

Since the late 1990s, various types of diagnostic kits to detect HIV have been developed. An immunological method using an antibody that recognizes a specific protein of HIV is one of the most widely used techniques for the diagnosis of HIV infection. Although the diagnostic accuracy of the immunological method using an antibody is high, it requires a large amount of a sample and it is essential to produce unique viral proteins or peptides in each disease in order to produce an antibody required for each diagnosis so that the manufacturing costs for preparing the antibody is increased. Furthermore, it is not easy to preserve and use proteins, and one or a limited number of types of diseases can be diagnosed at once. A method of diagnosing diseases by cultivating cells and using DNA probes can also be used. However, this method requires highly skilled professionals and a great deal of time. In order to overcome these drawbacks, research into various diagnostic kits using polymerase chain reaction (PCR) has been conducted. Demands for diagnostic kits using PCR are increasing due to their high accuracy, simplicity, and rapidity.

In particular, real-time PCR is one of the most widely used methods. Real-time PCR is a method of measuring the accumulation of PCR products in each cycle of PCR in real-time. Using the real-time PCR, fluorescent substances involved in reactions with the PCR products can be detected and the PCR products can be quantitatively calculated. While PCR products are identified using gel electrophoresis after a final stage of PCR is completed according to conventional PCR, real-time PCR does not require post-PCR gel electrophoresis, has high accuracy, sensitivity, and reproducibility, can be automated, can quantify the results, is quick, simple, and biologically safe against dyes such as ethidium bromide (EtBr) and UV irradiation, and can automatically identify amplification of specific genes. Thus, while only qualitative results are obtained using PCR or antigen/antibody methods, quantitative results with high specificity can be obtained using real-time PCR. In addition, since probes labeled with a fluorescence marker are used in real-time PCR, the amount of a sample can be reduced compared to that used in DNA chip and antigen/antibody reactions.

Therefore, there remains an unmet need in the art to both rapidly and accurately detect HIV infection and HIV genotype, and there is an unmet need in the art to develop a method of detecting HIV and a kit for detecting HIV using real-time PCR.

SUMMARY

According to an exemplary embodiment, a kit is provided for the detection of HIV-2 strains.

In one embodiment, a method is described for the real-time detection of HIV-2 strains in a sample.

According to an embodiment, a kit for the real-time detection of HIV-2 strains is provided, selected from the group consisting of the following primer sets and probes:

a primer set comprising a primer having the nucleotide sequence of SEQ ID NO: 1 and a primer having the nucleotide sequence of SEQ ID NO: 9 and a probe having the nucleotide sequence of SEQ ID NO: 10;

a primer set comprising a primer having the nucleotide sequence of SEQ ID NO: 2 and a primer having the nucleotide sequence of SEQ ID NO: 6 and a probe having the nucleotide sequence of SEQ ID NO: 10;

a primer set comprising a primer having the nucleotide sequence of SEQ ID NO: 2 and a primer comprising SEQ ID NO: 7 and a probe having the nucleotide sequence of SEQ ID NO: 10;

a primer set comprising a primer having the nucleotide sequence of SEQ ID NO: 2 and a primer having the nucleotide sequence of SEQ ID NO: 8 and a probe having the nucleotide sequence of SEQ ID NO: 10;

a primer set comprising a primer having the nucleotide sequence of SEQ ID NO: 2 and a primer having the nucleotide sequence of SEQ ID NO: 9 and a probe having the nucleotide sequence of SEQ ID NO: 10;

a primer set comprising a primer having the nucleotide sequence of SEQ ID NO: 3 and a primer having the nucleotide sequence of SEQ ID NO: 8 and a probe having the nucleotide sequence of SEQ ID NO: 10.

a primer set comprising a primer having the nucleotide sequence of SEQ ID NO: 4 and a primer having the nucleotide sequence of SEQ ID NO: 8 and a probe having the nucleotide sequence of SEQ ID NO: 10, and a primer set comprising a primer having the nucleotide sequence of SEQ ID NO: 5 and a primer having the nucleotide sequence of SEQ ID NO: 8 and a probe having the nucleotide sequence of SEQ ID NO: 10.

In an embodiment, a forward primer oligonucleotide includes an oligonucleotide of the sequence of SEQ ID NO: 11:

$X_1$CCAAGGAGTAGTAGAAGCAATGAATCACC$X_2$ (SEQ ID NO: 11), wherein $X_1$ is absence or G and $X_2$ is absence or A.

In an embodiment, a forward primer oligonucleotide includes an oligonucleotide of the sequence of SEQ ID NO: 12:

T$X_1$GTACTAATGGCAG$X_2$TCA$X_3$TGCATGAATT (SEQ ID NO: 12), wherein $X_1$ is A or T, $X_2$ is C or T and $X_3$ is C or T.

In another embodiment, the forward primer may be one selected from the group consisting of the oligonucleotides of SEQ ID NO: 1-5:

```
                                            (SEQ ID NO: 1)
       GCCAAGGAGTAGTAGAAGCAATGAATCACC, (SEQ ID NO: 2)
       GCCAAGGAGTAGTAGAAGCAATGAATCACCA, (SEQ ID NO: 3)
       CCAAGGAGTAGTAGAAGCAATGAATCACCA, (SEQ ID NO: 4)
       TAGTACTAATGGCAGTTCATTGCATGAATT,
       and (SEQ ID NO: 5)
       TTGTACTAATGGCAGCTCACTGCATGAATT.
```

In an embodiment, a reverse primer oligonucleotide includes an oligonucleotide of the sequence of SEQ ID NO: 13: $X_1X_2X_3X_4X_5X_6X_7X_8X_9X_{10}X_{11}$CTGCCTTCTCTG-AAATAGX$_{12}X_{13}X_{14}X_{15}X_{16}X_{17}X_{18}X_{19}X_{20}X_{21}X_{22}X_{23}$ (SEQ ID NO: 13), wherein $X_1$ is absence or A, $X_2$ is absence or C, $X_3$ is absence or A, $X_4$ is absence or G, $X_5$ is absence or C, $X_6$ is absence or T, $X_7$ is absence or G, $X_8$ is absence or A, $X_9$ is absence or T, $X_{10}$ is absence or C, $X_{11}$ is absence or T, $X_{12}$ is absence or A, $X_{13}$ is absence or C, $X_{14}$ is absence or C, $X_{15}$ is absence or C, $X_{16}$ is absence or G, $X_{17}$ is absence or A, $X_{18}$ is absence or A, $X_{19}$ is absence or A, $X_{20}$ is absence or A, $X_{21}$ is absence or T, $X_{22}$ is absence or T, and $X_{23}$ is absence or T.

In another embodiment, the reverse primer may be one selected from the group consisting of the oligonucleotides of SEQ ID NO: 6-9:

```
                                            (SEQ ID NO: 6)
       ACAGCTGATCTCTGCCTTCTCTGAAATAGA, (SEQ ID NO: 7)
       CAGCTGATCTCTGCCTTCTCTGAAATAGAC, (SEQ ID NO: 8)
       AGCTGATCTCTGCCTTCTCTGAAATAGACC,
       and (SEQ ID NO: 9)
       CTGCCTTCTCTGAAATAGACCCGAAAATTT.
```

In an embodiment, the probe may be the oligonucleotide sequence of SEQ ID: 10: TTAAAArGrArArGGIGAG-GAATAGGIG (SEQ ID NO: 10), wherein the nucleotides at positions 7, 8, 9 and 10 are ribonucleotides.

The probe may be coupled to a detectable label such as those described above, at one or both of its 3'-end and 5'-end.

In an embodiment, a kit containing a forward primer and a reverse primer, as described above, is provided. The kit further includes a probe as described above. Such kit is suitable and useful for an accurate, sensitive and fast detection of a target HIV-2 gene in a sample.

The kit may further contain a reverse transcriptase activity, polymerase activity, and a cleaving agent which is capable of cleaving an internal site of the probe oligonucleotides. The cleaving agent may be selected from the group consisting of an RNase H, an Kamchatka crab duplex specific nuclease, an endonuclease, and an nicking endonuclease. The kit may further contain uracil-N-glycosylase.

According to an embodiment, a method is described for the real-time detection of HIV-2 in a sample, including the steps of: providing a sample to be tested for the presence of HIV-2, extracting RNA from the sample; forming an amplification medium by mixing the RNA with a uracil-n-glycosylase, DNA polymerase, reverse transcriptase, appropriate deoxynucleoside triphosphates, a nucleic acid binding probe containing comprising a detectable marker with DNA and RNA nucleic acid sequences that are substantially complimentary to the HIV-2 target DNA, a reaction buffer, and an upstream primer and an downstream primer; incubating the amplification medium at a temperature and for a time sufficient to activate the uracil-N-glycosylase and cause the removal of carryover contaminating template nucleic acid; incubating the amplification medium at a temperature and for a time sufficient to inactivate the uracil-N-glycosylase and contact the RNA to a reverse transcriptase and a downstream primer to synthesize cDNA; incubating the amplification medium at a temperature and for a time sufficient to inactivate the reverse transcriptase and cause denaturation of the cDNA; thermally cycling the amplification medium between at least a denaturation temperature and an elongation temperature, wherein the upstream and downstream primers in combination amplify the target nucleic acid or a section thereof, wherein the section may be of any length provided that the section is unique to the HIV-2 genome; under conditions where the nucleic acid sequences within the probe can form a RNA:DNA heteroduplex with the complimentary DNA sequences in the PCR fragment of the HIV-2 target DNA; forming a reaction mixture of a target nucleic acid sequence and a plurality of nucleic acid probes which each include a detectable marker under conditions wherein the first nucleic acid probe of the plurality of nucleic acid probes including a first detectable marker is allowed to hybridize to the target nucleic acid or a section thereof; causing a change in the structure or conformation of the nucleic acid probe to activate the detectable marker; repeating steps (g) and (h) utilizing secondary nucleic acid probes from the plurality of nucleic acid probes within the reaction mixture, wherein a plurality of activated detectable markers are formed; and detecting a real-time increase in the emission of a signal from the label on the probe, wherein the increase in signal indicates the presence of the HIV-2 target DNA in the sample.

In one aspect, the real-time increase in the emission of the signal from the label on the probe results from the RNase H cleavage of the heteroduplex formed between the probe and one of the strands of the PCR fragment In another embodiment, the method may be used to determine the quantity of the HIV-2 RNA in a sample.

DETAILED DESCRIPTION OF THE INVENTION

Figure 1:
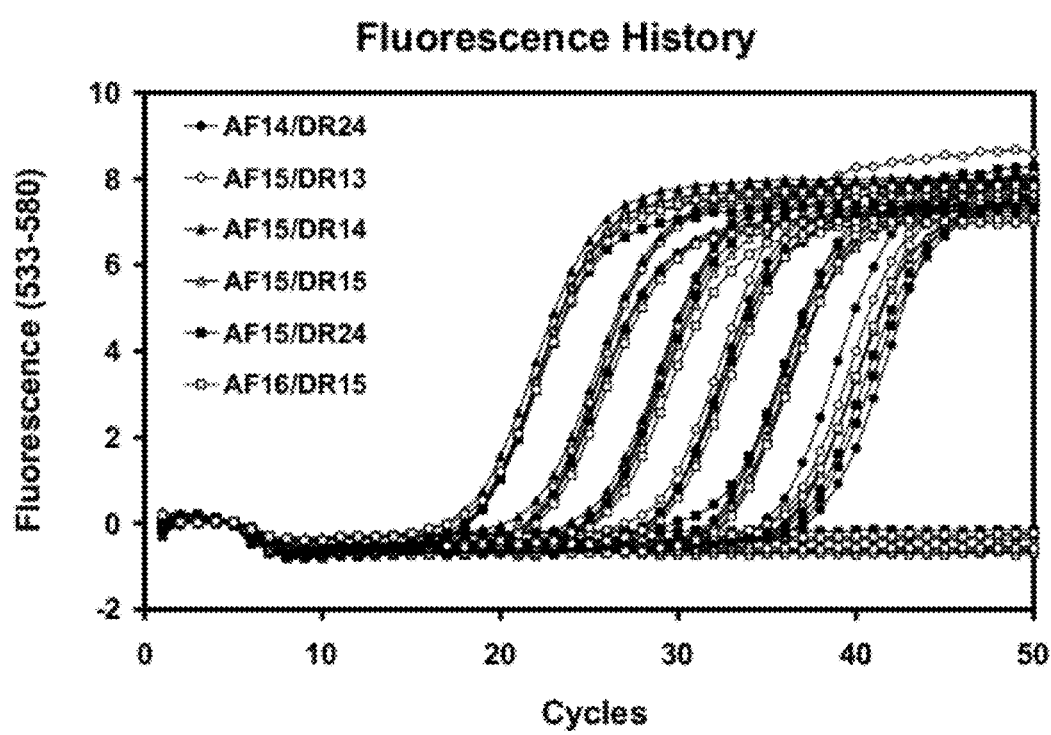
FIG. 1 shows amplification curves obtained by real-time polymerase chain reaction (PCR) of HIV-2 NIHZ using a kit according to an embodiment of the present invention.

The practice of the embodiments described herein employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

A "target DNA or "target RNA"" or "target nucleic acid," or "target nucleic acid sequence" refers to a nucleic acid that is targeted by DNA amplification. A target nucleic acid sequence serves as a template for amplification in a PCR reaction or reverse transcriptase-PCR reaction. Target nucleic acid sequences may include both naturally occurring and synthetic molecules. Exemplary target nucleic acid sequences include, but are not limited to, genomic DNA or genomic RNA.

The "nucleotide" used herein is a double-stranded or a single-stranded deoxyribonucleotide or ribonucleotide and includes nucleotide analogues unless otherwise stated.

The "probe" used herein is a natural or modified monomer or a linear oligomer which includes a deoxyribonucleotide and/or a ribonucleotide which may be hybridized with a specific polynucleotide sequence.

A probe according to an embodiment may include a sequence that is complementary to a polynucleotide that is a template and a substantially complementary sequence that does not inhibit specific hybridization. Conditions suitable for the hybridization are described above.

As used herein, the term "substantially complementary" refers to two nucleic acid strands that are sufficiently complimentary in sequence to anneal and form a stable duplex. The complementarity does not need to be perfect; there may be any number of base pair mismatches, for example, between the two nucleic acids. However, if the number of mismatches is so great that no hybridization can occur under even the least stringent hybridization conditions, the sequence is not a substantially complementary sequence. When two sequences are referred to as "substantially complementary" herein, it means that the sequences are sufficiently complementary to each other to hybridize under the selected reaction conditions. The relationship of nucleic acid complementarity and stringency of hybridization sufficient to achieve specificity is well known in the art. Two substantially complementary strands can be, for example, perfectly complementary or can contain from 1 to many mismatches so long as the hybridization conditions are sufficient to allow, for example discrimination between a pairing sequence and a non-pairing sequence. Accordingly, "substantially complementary" sequences can refer to sequences with base-pair complementarity of 100, 95, 90, 80, 75, 70, 60, 50 percent or less, or any number in between, in a double-stranded region.

The "substantially complementary sequence" used herein is a sequence that may be hybridized with the template polynucleotide under stringent conditions that are known in the art. The "stringent conditions" used herein are disclosed in Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985), and may be determined by controlling temperature, ionic strength (concentration of a buffer solution), and the existence of a compound such as an organic solvent. For example, the stringent conditions may be obtained by a) washing with a 0.015 M sodium chloride/0.0015 M sodium citrate/0.1% sodium dodecyl sulfate solution at 50° C., or b) hybridizing in a hybridization buffer solution including 50% formamide, 2×SSC and 10% dextran sulfate at 55° C. and washing with EDTA-containing 0.1×SSC at 55° C.

The "primer" used herein is a single-stranded oligonucleotide functioning as an origin of polymerization of template DNA under appropriate conditions (i.e., 4 types of different nucleoside triphosphates and polymerases) at a suitable temperature and in a suitable buffer solution.

The length of the primer may vary according to various factors, for example, temperature and the use of the primer, but the primer generally has 15 to 35 nucleotides. Generally, a short primer may form a sufficiently stable hybrid complex with its template at a low temperature. The "forward primer" and "reverse primer" are primers respectively binding to a 3' end and a 5' end of a specific region of a template that is amplified by PCR.

The sequence of the primer is not required to be completely complementary to a part of the sequence of the template. The primer may have sufficient complementarity to be hybridized with the template and perform intrinsic functions of the primer. Thus, a primer set according to an embodiment is not required to be completely complementary to the nucleotide sequence as a template. The primer set may have sufficient complementarity to be hybridized with the sequence and perform intrinsic functions of the primer.

The primer may be designed based on the nucleotide sequence of a polynucleotide as a template, for example, using a program for designing primers (PRIMER 3 program). Meanwhile, a primer according to an embodiment may be hybridized or annealed to a part of a template to form a double-strand. Conditions for hybridizing nucleic acid suitable for forming the double-stranded structure are disclosed by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D. C. (1985)

HIV-2 strains that are members of a retrovirus family are known as pathogens of AIDS. HIV-related opportunistic infections attack and destroy the human immune system, thus threatening life. The HIV-2 strains may be HIV-2 NIHZ, but are not limited thereto.

According to an embodiment, HIV-2-specific primers that detect various types of HIV-2 strains are prepared such that amplification products have a size of 50 to 200 bp suitable for real-time PCR.

In the primer sets and probes for detecting HIV-2 strains according to an embodiment, the probe may be labeled with different detectable markers. The detectable marker indicates a compound, a biological molecule, biological molecule analogues, or the like which are linked, bound, or attached to the probe so as to identify density, concentration, quantity, or the like using various methods known in the art. For example, the detectable marker may be a fluorescence marker, a luminescent material, a bioluminescent material, an isotope, or the like, but is not limited thereto. According to an embodiment, the 5' end of the probe may be labeled with one fluorescence marker selected from the group consisting of FAM, VIC, TET, JOE, HEX, CY3, CY5, ROX, RED610, TEXAS RED, RED670, TYE563, and NED, and the 3' end of the probe may be labeled with one fluorescence quencher selected from the group consisting of 6-TAMRA, BHQ-1,2,3, Iowa Black RQ-Sp, and a molecular grove binding non-fluorescence quencher (MGBNFQ). The fluorescence marker is commercially available and can be procured without difficulty. Excitation and emission wavelengths vary according to the type of the fluorescence marker, and the use of the fluorescence marker also varies. The probe may be labeled with the fluorescence marker using various methods that are known in the art. A CataCleave™ probe according to an embodiment may have the 5' end labeled with a fluorescence marker, e.g., TYE™ 563 and the 3' end labeled with a fluorescence quencher, e.g., Iowa Black™ RQ-Sp, and may be added to a PCR reaction solution.

According to an embodiment, the probe may be a CataCleave probe. CataCleave™ technology differs from TaqMan™ in that cleavage of a probe is accomplished by a second enzyme, i.e., RNase H, which does not have DNA polymerase activity. The CataCleave™ probe has a nucleotide sequence, i.e., cleavage site, within a molecule which is a target of an endonuclease, such as a restriction enzyme or RNase. According to an embodiment, the CataCleave™ probe has a chimeric structure where the 5' and 3' ends of the probe are constructed of DNA and the cleavage site contains RNA. The DNA sequence portions of the probe are labeled with a fluorescence resonance energy transfer (FRET) pair either at the ends or internally. In a real-time PCR including a CataCleave™ probe, PCR reaction includes an RNase H enzyme that will specifically cleave the RNA sequence portion of a RNA-DNA duplex. When the RNA sequence portion of the probe is cleaved by the enzyme, the two parts of the probe, i.e., a donor and an acceptor, dissociate from a target amplicon at a reaction temperature and diffuse into a reaction buffer. As the donor and acceptor separate, FRET is reversed in the same way as a TaqMan™ probe and donor emission can be monitored. Cleavage and dissociation regenerates a site for further CataCleave™ probe binding on the amplicon. In this way, it is possible for a single amplicon to serve as a target or multiple rounds of probe cleavage until the primer is extended through the CataCleave™ probe binding site. Meanwhile, the CataCleave™ probe is disclosed in detail in *Anal. Biochem.* 333:246-255, 2004 and U.S. Pat. No. 6,787,304, the contents of which are entirely incorporated herein by reference.

As used herein, the term "oligonucleotide" is used sometimes interchangeably with "primer" or "polynucleotide."

Oligonucleotides may be synthesized and prepared by any suitable methods (such as chemical synthesis), which are known in the art. Oligonucleotides may also be conveniently available through commercial sources.

The terms "annealing" and "hybridization" are sometimes used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

A person of skill in the art will know how to design PCR primers flanking a HIV-2 genomic sequence of interest. Synthesized oligos are typically between 20 and 26 base pairs in length with a melting temperature, $T_M$ of around 55 degrees.

As used herein, "label" or "detectable label" can refer to any chemical moiety attached to a nucleotide, nucleotide polymer, or nucleic acid binding factor, wherein the attachment may be covalent or non-covalent. Preferably, the label is detectable and renders said nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

The DNA polymerase may be a thermally stable DNA polymerase obtained from *Thermus aquaticus* (Taq), *Thermus thermophilus* (Tth), *Thermus filiformis, Thermis flavus, Thermococcus literalis*, or *Pyrococcus furiosus* (Pfu). In addition, RNase H includes a thermally stable RNase H enzyme such as *Pyrococcus furiosus* RNase H II, *Pyrococcus horikoshi* RNase H II, *Thermococcus litoralis* RNase HI, or *Thermus thermophilus* RNase HI, but is not limited thereto. The buffer solution is added to amplification to change stability, activity and/or lifetime of at least one component involved in the amplification reaction by controlling the pH of the amplification reaction. The buffer solution is well known in the art and may be Tris, Tricine, MOPS, or HEPES, but is not limited thereto. The kit may further include a dNTP mixture (dATP, dCTP, dGTP, and dTTP) and a DNA polymerase cofactor. The primer set and probe may be packed in a single reaction container, strip, or microplate by using various methods known in the art.

According to another embodiment, there is provided a method of detecting HIV-2 strains, the method including: isolating total RNA from a sample; performing a real-time PCR by mixing the isolated total RNA and the kit; and identifying the existence of HIV-2 strains based on the results of the real-time PCR.

The method of detecting HIV-2 strains will now be described in more detail. First, the method includes isolating total RNA from a sample. The method may be applied to a sample that is assumed to be infected with HIV-2 strains. The sample may include cultured cells and animal or human blood, plasma, serum, sperm, or mucus, but is not limited thereto. The isolation of RNA may be accomplished by various methods known in the art. The methods are disclosed in detail in Joseph Sambrook, et al., *Molecular Cloning, A Laboratory Manual*, Cold Spring Harbor Laboratory Press, Cold Spring Harbor, N.Y. (2001), of which contents are entirely incorporated herein by reference.

Second, the method includes performing a real-time PCR by mixing the isolated total RNA and the kit.

According to an embodiment, the method may further include performing a reverse transcription of the isolated total RNA before performing the real-time PCR. Since the method is used to detect HIV-2 strains that are RNA viruses, the isolated RNA needs to be converted into DNA as a template used in the real-time PCR. The reverse transcription may be conducted using various reverse transcriptases that are known in the art.

According to an embodiment, the kit for detecting HIV-2 strains may be used by using various methods and by using various devices for real-time PCR that are known in the art. The real-time PCR is a method of detecting fluorescence that is emitted in every cycle of PCR by a DNA polymerase and based on the FRET principle and quantifying the fluorescence in real-time using a device equipped with a thermal cycler and a spectrofluorophotometer. Using the real-time PCR, specific amplification products are distinguished from non-specific amplification products, and results of analysis may be automatically obtained without difficulty. The device used for the real-time PCR may include real-time PCR systems 7900, 7500, and 7300 (Applied Biosystems), Mx3000p (Stratagene), Chromo 4 (BioRad), and Roche Lightcycler 480, but is not limited thereto. While performing PCR, the real-time PCR device senses the change in fluorescence of the probe specific for the amplified PCR products to show curves as shown in FIG. 1.

In the method of detecting HIV-2 strains according to an embodiment, the real-time PCR may be performed using various methods that are known in the art. For example, an initial denaturation is performed at 95° C. for 10 minutes, and then a denaturation (at 95° C. for 10 seconds), an annealing and RNase HII reaction (at 55° C. for 10 seconds), and an elongation (at 72° C. for 30 seconds) are repeated 60 times. HIV-2 strains that can be detected using the method are described above.

Finally, the method includes identifying the existence of HIV-2 strains based on the results of the real-time PCR.

The existence of HIV-2 strains may be identified by calculating a $C_t$ value that is the number of cycles when the amount of the amplified PCR products reaches a predetermined level, based on the curve of the fluorescence marker labeled in the probe of the amplified PCR products obtained by the real-time PCR. If the $C_t$ value is in the range of 15 to 50, or 20 to 45, it can be concluded that HIV-2 strains exist. Meanwhile, the $C_t$ value may be automatically calculated by a program of the real-time PCR device.

According to the kit for detecting HIV-2 strains and the method of detecting HIV-2 strains by using the kit, the results of the detection can be rapidly identified with a reduced number of copies of a sample in real-time.

The previously described embodiments have many advantages, including the ability to detect HIV-2 nucleic acid sequences in a sample in real-time. The detection method is fast, accurate and suitable for high throughput applications.
Amplification Once the nucleic acid is isolated from a sample and the primers are selected, nucleic acid amplification can be accomplished by a variety of methods, including the polymerase chain reaction (PCR), nucleic acid sequence based amplification (NASBA), ligase chain reaction (LCR), and rolling circle amplification (RCA). The polymerase chain reaction (PCR) is the method most commonly used to amplify specific target DNA sequences.

"Polymerase chain reaction," or "PCR," generally refers to a method for amplification of a desired nucleotide sequence in vitro. The procedure is described in detail in U.S. Pat. Nos. 4,683,202, 4,683,195, 4,800,159, and 4,965,188, the contents of which are hereby incorporated herein in their entirety. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers.

One of the most widely used techniques to study gene expression exploits first-strand cDNA for mRNA sequence(s) as template for amplification by the PCR. This method, often referred to as reverse transcriptase-PCR, exploits the high sensitivity and specificity of the PCR process and is widely used for detection and quantification of RNA.

The reverse transcriptase-PCR procedure, carried out as either an end-point or real-time assay, involves two separate molecular syntheses: (i) the synthesis of cDNA from an RNA template; and (ii) the replication of the newly synthesized cDNA through PCR amplification. To attempt to address the technical problems often associated with reverse transcriptase-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcriptase-PCR procedure (e.g., two step reverse transcriptase-PCR), reverse transcription is performed as an independent step using the optimal buffer condition for reverse transcriptase activity. Following cDNA synthesis, the reaction is diluted to decrease $MgCl_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" reverse transcriptase PCR methods use a common buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{2+}$ then PCR is carried out in the presence of $Mg^{2+}$ after the removal of $Mn^{2+}$ by a chelating agent. Finally, the "continuous" method (e.g., one step reverse transcriptase-PCR) integrates the three reverse transcriptase-PCR steps into a single continuous reaction that avoids the opening of the reaction tube for component or enzyme addition. Continuous reverse transcriptase-PCR has been described as a single enzyme system using the reverse transcriptase activity of thermostable Taq DNA Polymerase and Tth polymerase and as a two enzyme system using AMV reverse transcriptase and Taq DNA Polymerase wherein the initial 65° C. RNA denaturation step was omitted.

The first step in real-time, reverse-transcription PCR is to generate the complementary DNA strand using one of the template specific DNA primers. In traditional PCR reactions this product is denatured, the second template specific primer binds to the cDNA, and is extended to form duplex DNA. This product is amplified in subsequent rounds of temperature cycling. To maintain the highest sensitivity it is important that the RNA not be degraded prior to synthesis of cDNA. The presence of RNase H in the reaction buffer will cause unwanted degradation of the RNA:DNA hybrid formed in the first step of the process because it can serve as a substrate for the enzyme. There are two major methods to combat this issue. One is to physically separate the RNase H from the rest of the reverse-transcription reaction using a barrier such as wax that will melt during the initial high temperature DNA denaturation step. A second method is to modify the RNase H such that it is inactive at the reverse-transcription temperature, typically 45-55° C. Several methods are known in the art, including reaction of RNase H with an antibody, or reversible chemical modification. Various RNase H which may be employed in the above described method will be explained in more detail hereinafter.

Additional examples of RNase H enzymes that can be employed in the invention are described in U.S. Patent Application No. 2009/0325169 to Walder et al.

One step reverse transcriptase-PCR provides several advantages over uncoupled reverse transcriptase-PCR. One step reverse transcriptase-PCR requires less handling of the reaction mixture reagents and nucleic acid products than uncoupled reverse transcriptase-PCR (e.g., opening of the reaction tube for component or enzyme addition in between the two reaction steps), and is therefore less labor intensive, reducing the required number of person hours. One step reverse transcriptase-PCR also requires less sample, and reduces the risk of contamination. The sensitivity and specificity of one-step reverse transcriptase-PCR has proven well suited for studying expression levels of one to several genes in a given sample or the detection of pathogen RNA. Typically, this procedure has been limited to use of gene-specific primers to initiate cDNA synthesis.

The ability to measure the kinetics of a PCR reaction by real-time detection in combination with these reverse transcriptase-PCR techniques has enabled accurate and precise determination of RNA copy number with high sensitivity. This has become possible by detecting the reverse transcriptase-PCR product through fluorescence monitoring and measurement of PCR product during the amplification process by fluorescent dual-labeled hybridization probe technologies, such as the 5' fluorogenic nuclease assay ("TaqMan") or endonuclease assay ("CataCleave™").

Real-time methods have been developed to monitor amplification during the PCR process. These methods typically employ fluorescently labeled probes that bind to the newly synthesized DNA or dyes whose fluorescence emission is increased when intercalated into double stranded DNA.

Real-Time PCR of an HIV-2 Target Nucleic Acid Sequence Using a CataCleave™ Probe The probes are generally designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM, TAMRA, VIC, JOE, Cy3, Cy5, and Texas Red. Acceptor chromophores are chosen so that their excitation spectra overlap with the emission spectrum of the donor. An example of such a pair is FAM-TAMRA. There are also non fluorescent acceptors that will quench a wide range of donors. Other examples of appropriate donor-acceptor FRET pairs will be known to those skilled in the art.

Common examples of FRET probes that can be used for real-time detection of PCR include molecular beacons, TaqMan probes (e.g., U.S. Pat. Nos. 5,210,015 and 5,487,972), and CataCleave™ probes (e.g., U.S. Pat. No. 5,763,181). The molecular beacon is a single stranded oligonucleotide designed so that in the unbound state the probe forms a secondary structure where the donor and acceptor chromophores are in close proximity and donor emission is reduced. At the proper reaction temperature the beacon unfolds and specifically binds to the amplicon. Once unfolded the distance between the donor and acceptor chromophores increases such that FRET is reversed and donor emission can be monitored using specialized instrumentation. TaqMan and CataCleave™ technologies differ from the molecular beacon in that the FRET probes employed are cleaved such that the donor and acceptor chromophores become sufficiently separated to reverse FRET.

TaqMan technology employs a single stranded oligonucleotide probe that is labeled at the 5' end with a donor chromophore and at the 3' end with an acceptor chromophore. The DNA polymerase used for amplification must contain a 5'→3' exonuclease activity. The TaqMan probe binds to one strand of the amplicon at the same time that the primer binds. As the DNA polymerase extends the primer the polymerase will eventually encounter the bound TaqMan probe. At this time the exonuclease activity of the polymerase will sequentially degrade the TaqMan probe starting at the 5' end. As the probe is digested the mononucleotides comprising the probe are released into the reaction buffer. The donor diffuses away from the acceptor and FRET is reversed. Emission from the donor is monitored to identify probe cleavage. Because of the way TaqMan works a specific amplicon can be detected only once for every cycle of PCR. Extension of the primer through the TaqMan target site generates a double stranded product that prevents further binding of TaqMan probes until the amplicon is denatured in the next PCR cycle.

U.S. Pat. No. 5,763,181, the content of which is incorporated herein by reference, describes another real-time detection method (referred to as "CataCleave™"). CataCleave™ technology differs from TaqMan in that cleavage of the probe is accomplished by a second enzyme that does not have polymerase activity. The CataCleave™ probe has a sequence within the molecule which is a target of an endonuclease, such as, for example a restriction enzyme or RNase. In one example, the CataCleave™ probe has a chimeric structure where the 5' and 3' ends of the probe are constructed of DNA and the cleavage site contains RNA. The DNA sequence portions of the probe are labeled with a FRET pair either at the ends or internally. The PCR reaction includes an RNase H enzyme that will specifically cleave the RNA sequence portion of a RNA-DNA duplex. After cleavage, the two halves of the probe dissociate from the target amplicon at the reaction temperature and diffuse into the reaction buffer. As the donor and acceptors separate FRET is reversed in the same way as the TaqMan probe and donor emission can be monitored. Cleavage and dissociation regenerates a site for further CataCleave™ binding. In this way it is possible for a single amplicon to serve as a target or multiple rounds of probe cleavage until the primer is extended through the CataCleave™ probe binding site.

Labeling of a HIV 2-Specific CataCleave™ Probe

The term "probe" comprises a polynucleotide that comprises a specific portion designed to hybridize in a sequence-specific manner with a complementary region of a specific nucleic acid sequence, e.g., a target nucleic acid sequence. In one embodiment, the oligonucleotide probe is in the range of 15-60 nucleotides in length. More preferably, the oligonucleotide probe is in the range of 18-45 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the references describing Taq-man assays or CataCleave™, described in U.S. Pat. Nos. 5,763,181, 6,787,304, and 7,112,422, the contents of which contents are incorporated herein by reference in their entirety.

As used herein, a "label" or "detectable label" may refer to any label of a CataCleave™ probe comprising a fluorochrome compound that is attached to the probe by covalent or non-covalent means.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides light that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention. A fluorochrome and fluorescent quencher may include, but not be limited to, ALEXA FLOUR® 350, ALEXA FLOUR® 430, ALEXA FLOUR® 488, ALEXA FLOUR® 532, ALEXA FLOUR® 546, ALEXA FLOUR® 568, ALEXA FLOUR® 594, ALEXA FLOUR® 633, ALEXA FLOUR® 647, ALEXA FLOUR® 660, ALEXA FLOUR® 680, 7-diethylaminocoumarin-3-carboxylic acid, Fluorescein, OREGON GREEN® 488, OREGON GREEN® 514, tetramethylrhodamine, Rhodamine X, TEXAS RED® dye (sulforhodamine 101 acid chloride), Dabcyl, BODIPY® FL, BODIPY® 630/650, BODIPY® 6501665, BODIPY® TMR-X, BODIPY® TR-X, dialkylaminocoumarin, Cy5.5, Cy5, Cy3.5, Cy3, DTPA($Eu^{3+}$)-AMCA and TTHA($Eu^{3+}$) AMCA.

In one embodiment, the 3' terminal nucleotide of the oligonucleotide probe is blocked or rendered incapable of extension by a nucleic acid polymerase. Such blocking is conveniently carried out by the attachment of a reporter or quencher molecule to the terminal 3' position of the probe.

In one embodiment, reporter molecules are fluorescent organic dyes derivatized for attachment to the terminal 3' or terminal 5' ends of the probe via a linking moiety. Preferably, quencher molecules are also organic dyes, which may or may not be fluorescent, depending on the embodiment of the invention. For example, in a preferred embodiment of the invention, the quencher molecule is non-fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In one embodiment, reporter and quencher molecules are selected from fluorescein and non-fluorescent quencher dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Rhodamine and non-fluorescent quencher dyes are also conveniently attached to the 3' end of an oligonucleotide at the beginning of solid phase synthesis, e.g., Woo et al., U.S. Pat. No. 5,231,191; and Hobbs, Jr., U.S. Pat. No. 4,997,928.

Attachment of a HIV-2-Specific CataCleave™ Probe to a Solid Support

In one embodiment of the invention, the oligonucleotide probe can be attached to a solid support. Different probes may be attached to the solid support and may be used to simultaneously detect different target sequences in a sample. Reporter molecules having different fluorescence wavelengths can be used on the different probes, thus enabling hybridization to the different probes to be separately detected.

Examples of preferred types of solid supports for immobilization of the oligonucleotide probe include polystyrene, avidin coated polystyrene beads cellulose, nylon, acrylamide gel and activated dextran, controlled pore glass (CPG), glass plates and highly cross-linked polystyrene. These solid supports are preferred for hybridization and diagnostic studies because of their chemical stability, ease of functionalization and well defined surface area. Solid supports such as controlled pore glass (500 Å, 1000 Å) and non-swelling high cross-linked polystyrene (1000 Å) are particularly preferred in view of their compatibility with oligonucleotide synthesis.

The oligonucleotide probe may be attached to the solid support in a variety of manners. For example, the probe may be attached to the solid support by attachment of the 3' or 5' terminal nucleotide of the probe to the solid support. However, the probe may be attached to the solid support by a linker which serves to distance the probe from the solid support. The linker is most preferably at least 30 atoms in length, more preferably at least 50 atoms in length.

Hybridization of a probe immobilized to a solid support generally requires that the probe be separated from the solid support by at least 30 atoms, more-preferably at least 50 atoms. In order to achieve this separation, the linker generally includes a spacer positioned between the linker and the 3' nucleoside. For oligonucleotide synthesis, the linker arm is usually attached to the 3'-OH of the 3' nucleoside by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred because it is commercially available, soluble in both organic and aqueous media, easy to functionalize, and is completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages. Immobilization of a probe is well known in the art and one skilled in the art may determine the immobilization conditions.

According to one embodiment of the method, the hybridization probe is immobilized on a solid support. The oligonucleotide probe is contacted with a sample of nucleic acids under conditions favorable for hybridization. In an unhybridized state, the fluorescent label is quenched by the quencher. On hybridization to the target, the fluorescent label is separated from the quencher resulting in fluorescence.

Immobilization of the hybridization probe to the solid support also enables the target sequence hybridized to the probe to be readily isolated from the sample. In later steps, the isolated target sequence may be separated from the solid support and processed (e.g., purified, amplified) according to methods well known in the art depending on the particular needs of the researcher.

Real-Time Detection of HIV-2 Target Nucleic Acid Sequences Using a CataCleave™ Probe The labeled oligonucleotide probe may be used as a probe for the real-time detection of HIV-2 target nucleic acid sequence in a sample.

A CataCleave™ oligonucleotide probe is first synthesized with DNA and RNA sequences that are complimentary to sequences found within a PCR amplicon comprising a selected HIV-2 target sequence. In one embodiment, the probe is labeled with a FRET pair, for example, a fluorescein molecule at one end of the probe and a non-fluorescent quencher molecule at the other end. Hence, upon hybridization of the probe with the PCR amplicon, a RNA:DNA heteroduplex forms that can be cleaved by an RNase H activity.

RNase H hydrolyzes RNA in RNA-DNA hybrids. This enzyme was first identified in calf thymus but has subsequently been described in a variety of organisms. RNase H activity appears to be ubiquitous in eukaryotes and bacteria. Although RNase H's constitute a family of proteins of varying molecular weight and nucleolytic activity, substrate requirements appear to be similar for the various isotypes. For example, most RNase H's studied to date function as endonucleases and requiring divalent cations (e.g., $Mg^{2+}$, $Mn^{2+}$) to produce cleavage products with 5' phosphate and 3' hydroxyl termini.

RNase HI from *E. coli* is the best-characterized member of the RNase H family. In addition to RNase HI, a second *E. coli* RNase H, RNase HII has been cloned and characterized (Itaya, M., Proc. Natl. Acad. Sci. USA, 1990, 87, 8587-8591). It is comprised of 213 amino acids while RNase HI is 155 amino acids long. *E. coli* RNase HIM displays only 17% homology with *E. coli* RNase HI. An RNase H cloned from *S. typhimurium* differed from *E. coli* RNase HI in only 11 positions and was 155 amino acids in length (Itaya, M. and Kondo K., Nucleic Acids Res., 1991, 19, 4443-4449).

Proteins that display RNase H activity have also been cloned and purified from a number of viruses, other bacteria and yeast (Wintersberger, U. Pharmac. Ther., 1990, 48, 259-280). In many cases, proteins with RNase H activity appear to be fusion proteins in which RNase H is fused to the amino or carboxy end of another enzyme, often a DNA or RNA polymerase. The RNase H domain has been consistently found to be highly homologous to *E. coli* RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., Eur. J. Biochem., 1977, 74, 203-208). RNase HI enzymes are reported to have molecular weights in the 68-90 kDa range, be activated by either $Mn.sup.2+$ or $Mg.sup.2+$ and be insensitive to sulfhydryl agents. In contrast, RNase H II enzymes have been reported to have molecular weights ranging from 31-45 kDa, to require $Mg^{2+}$ to be highly sensitive to sulfhydryl agents and to be inhibited by $Mn^{2+}$ (Busen, W., and Hausen, P., Eur. J. Biochem., 1975, 52, 179-190; Kane, C. M., Biochemistry, 1988, 27, 3187-3196; Busen, W., J. Biol. Chem., 1982, 257, 7106-7108).

An enzyme with RNase HII characteristics has been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini.

According to an embodiment, real-time nucleic acid amplification is performed on a target polynucleotide in the presence of a thermostable nucleic acid polymerase, an RNase H activity, a pair of PCR amplification primers capable of hybridizing to the HIV-2 target polynucleotide, and the labeled CataCleave™ oligonucleotide probe. During the real-time PCR reaction, cleavage of the probe by RNase H leads to the separation of the fluorescent donor from the fluorescent quencher and results in the real-time increase in fluorescence of the probe corresponding to the real-time detection of HIV-2 target DNA sequences in the sample.

In certain embodiments, the real-time nucleic acid amplification permits the real-time detection of a single target DNA molecule in less than about 40 PCR amplification cycles.

Exemplary Real-Time Detection of HIV-2 Gene Sequences in a Sample

First, the method includes isolating total RNA from a sample. The method may be applied to a sample that is assumed to be infected with HIV-2. The sample may include cultured cells and animal or human blood, plasma, serum, sperm, or mucus, but is not limited thereto. The isolation of RNA may be accomplished by various methods known in the art. The methods are disclosed in detail in Joseph Sambrook, et al., *Molecular Cloning, A Laboratory Manual*, Cold Spring Harbor Laboratory Press, Cold Spring Harbor, N.Y. (2001), of which contents are entirely incorporated herein by reference.

Second, the method includes performing real-time PCR by mixing the isolated total RNA and associated reaction components.

According to an embodiment, the method may further include performing a reverse transcription of the isolated total RNA before performing the real-time PCR. Since the method is used to detect the RNA virus HIV-2, the isolated RNA needs to be converted into cDNA so that it can be used as a template in real-time PCR. The reverse transcription may be conducted using various reverse transcriptases such as those purified from Avian Myeloblastosis Virus (AMV) or Moloney Murine Leukemia Virus (MMLV) or others that are known in the art.

According to an embodiment, instruments for performing temperature cycling and real time detection of the resultant specific amplified products are available commercially. Examples of such instruments include the 7900, 7500, and 7300 real-time PCR systems (Applied Biosystems Incorporated), Mx3000p (Stratagene), Chromo 4 (BioRad), and Roche Lightcycler 480, but are not limited thereto. While performing real time PCR, these devices monitor changes in emission intensity from the detectable marker and convert that information to graphical and/or numerical information that can be analyzed to determine if the target template is present in the test sample.

In the method of detecting HIV-2 according to an embodiment, the real-time PCR may be performed using various methods that are known in the art. For example, an initial denaturation is performed at 95° C. for 10 minutes, and then a denaturation (at 95° C. for 10 seconds), an annealing and RNase II reaction (at 55° C. for 10 seconds), and an elongation (at 72° C. for 30 seconds) are repeated 60 times. Different groups of HIV-2 that can be detected using the method are described above.

Finally, the method includes identifying the existence of HIV-2 based on the results of the real-time PCR.

The existence of HIV-2 may be identified by calculating a $C_t$ value that is the number of amplification cycles when the emission intensity from the detectable marker reaches a predetermined threshold level. If the $C_t$ value is in the range of 10 to 45, it can be concluded that the sample was contaminated with HIV-2. The $C_t$ value may be automatically calculated by a program of the real-time PCR device.

The present invention will be described in further detail with reference to the following examples. These examples are for illustrative purposes only and are not intended to limit the scope of the invention.

The enzyme "Hot Start" RNase HII used in the Examples is a reversibly modified RNase HII. When the modified enzyme is used in a reaction with a Tris based buffer and the temperature is raised to 95° C. the pH of the solution drops and RNase H activity is restored. This method allows for the inclusion of RNase H in the reaction mixture prior to the initiation of reverse transcription. RNase HII and is described in more detail in a co-pending application No. 61/347,984 filed May 25, 2010, the disclosure of which is incorporated herein by reference in its entirety.

Table 1 below depicts the sequences of primers and probes.

Table 2 depicts $C_t$ values (the numbers of cycles when the amount of the PCR products increased to a predetermined level) based on the amplification curves of FIG. 1.

Figure 2:
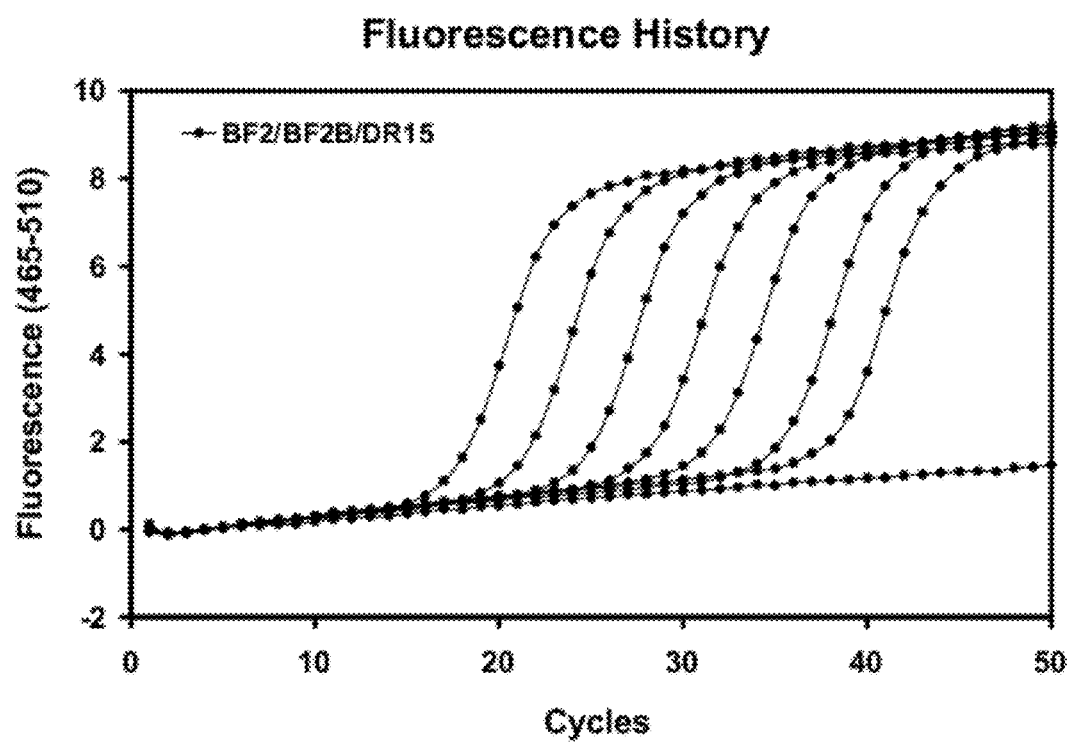
FIG. 2 shows amplification curves obtained by real-time polymerase chain reaction (PCR) of HIV-2 NIHZ using a kit according to an embodiment of the present invention.

Table 3 depicts $C_t$ values (the numbers of cycles when the amount of the PCR products increased to a predetermined level) based on the amplification curves of FIG. 2

EXAMPLES

The present invention will be described in further detail with reference to the following examples. These examples are for illustrative purposes only and are not intended to limit the scope of the invention.

Example 1

Preparation of Primer and Probe for Real-Time Detection of HIV-2

It was identified that primer used for real-time detection of HIV-2 has a nucleotide sequence capable of amplifying only a part of a HIV-2A NIHZ pol gene (GenBank accession number: J03654.1, GI:1332359). The nucleotide sequence was identified by obtaining nucleotide sequences of pol gene, which is a gene for a non-structural protein, from genes of HIV-2A NIHZ, selecting a primer set to be used in a real-time PCR by using Beacon Designer Software (Premier Biosoft International) and analyzing a nucleotide of the selected primer using a basic local alignment search tool (BLAST).

A CataCleave™ probe that specifically binds to a template of polymerase chain reaction (PCR) was prepared as the probe to detect the amount of PCR products that increases in real-time during real-time PCR. Since the amount of PCR products is detected using fluorescence emitted from the probe during PCR, and the probe has a higher sensitivity than gel electrophoresis that is conventionally used to identify PCR products. The probe was selected from the nucleotide sequences of the HIV-2A NIHZ pol gene that is a template amplified by the primer set in the same manner as in the preparation of the primer. The 5' end of the probe was labeled with TYE™ 563 and the 3' end of the probe was labeled with Iowa Black™ RQ-Sp. The determined primer and probe were synthesized by Roche Co., Ltd.

Exemplary nucleotide sequences of the primers and probes used herein are shown in Table 1 below.

TABLE 1

| SEQ ID NO: | Primer/Probe | Sequence (5'-3') |
|---|---|---|
| 1 | AF14 | GCCAAGGAGTAGTAGAAGCAATGAATCACC |
| 2 | AF15 | GCCAAGGAGTAGTAGAAGCAATGAATCACCA |
| 3 | AF16 | CCAAGGAGTAGTAGAAGCAATGAATCACCA |
| 4 | BF2 | TAGTACTAATGGCAGTTCATTGCATGAATT |
| 5 | BF2B | TTGTACTAATGGCAGCTCACTGCATGAATT |
| 6 | DR13 | ACAGCTGATCTCTGCCTTCTCTGAAATAGA |
| 7 | DR14 | CAGCTGATCTCTGCCTTCTCTGAAATAGAC |
| 8 | DR15 | AGCTGATCTCTGCCTTCTCTGAAATAGACC |
| 9 | DR24 | CTGCCTTCTCTGAAATAGACCCGAAAATTT |
| 10 | HIV2-P2 | TYE563/TTAAAArGrArArGGIGAGGAATAGGIG/IAbRQSp |
| 11 | FPX | $X_1$CCAAGGAGTAGTAGAAGCAATGAATCACC$X_2$ |
| 12 | FPX2 | T$X_1$GTACTAATGGCAG$X_2$TCA$X_3$TGCATGAATT |
| 13 | RPX | $X_1X_2X_3X_4X_5X_6X_7X_8X_9X_{10}X_{11}$CTGCCTTCTCTGAAATAG$X_{12}X_{13}X_{14}X_{15}X_{16}X_{17}X_{18}X_{19}X_{20}X_{21}X_{22}X_{23}$ |

In the above Table 1, the probe of SEQ ID NO: 9 is shown as having a detectable label at each of 5' and 3' ends thereof, and the nucleotides "rA" and "rG" are ribonucleotides. Furthermore, TYE563 is TYE™ 563, and IAbRQSp is Iowa Black™ RQ-Sp for short wavelength emission.

For SEQ ID NO: 11, $X_1$ is absence or G and $X_2$ is absence or A.

For SEQ ID NO: 12, $X_1$ is A or T, $X_2$ is C or T and $X_3$ is C or T.

For SEQ ID NO: 13, $X_1$ is absence or A, $X_2$ is absence or C, $X_3$ is absence or A, $X_4$ is absence or G, $X_5$ is absence or C, $X_6$ is absence or T, $X_7$ is absence or G, $X_8$ is absence or A, $X_9$ is absence or T, $X_{10}$ is absence or C, $X_{11}$ is absence or T, $X_{12}$ is absence or A, $X_{13}$ is absence or C, $X_{14}$ is absence or C, $X_{15}$ is absence or C, $X_{16}$ is absence or G, $X_{17}$ is absence or A, $X_{18}$ is absence or A, $X_{19}$ is absence or A, $X_{20}$ is absence or A, $X_{21}$ is absence or T, $X_{22}$ is absence or T, and $X_{23}$ is absence or T.

Example 2

Method of Detecting HIV-2 Using Real-Time PCR

Total RNA of HIV-2 that is used as a template in real-time PCR was subjected to extraction using Trizol reagent (Invitrogen).

A mixture including 10 μl of RNA and 15 μl of Cata-Cleave™ master mix (25 μl total reaction volume) was used for all real-time RCRs performed herein. The CataCleave™ master mix 135 μl included 112.5 μl of a buffer solution (32 mM HEPES (4-(2-hydroxyethyl)-1-(piperazineethane-sulfonic acid))-KOH, pH 7.8, 100 mM potassium acetate, 4 mM magnesium acetate, 0.11% bovine serum albumin, and 1% dimethyl sulfoxide), 0.675 μl of 100 μM forward primer (SEQ ID NO: 1, 2, 3, r 4, or 5), 0.675 μl of 100 μM reverse primer (SEQ ID NO: 6, 7, 8, or 9), 0.45 μl of 25 μM Cata-Cleave™ probe (SEQ ID NO: 10), 1.125 μl of SYBR Green I, 9 μl of dNTP mix (10 mM dGTP, dCTP, dATP, and dTTP), 4.5 μl of Platinum® Taq DNA polymerase (Invitrogen), 4.5 μl of Pfu RNase HII, 0.45 μl of Superscript® reverse transcriptase (Invitrogen), and 1.125 μl of distilled water.

cDNA was synthesized using the RNA as a template by performing a reverse transcription (first reaction) of the reactants at 50° C. for 15 minutes and denaturing the sample at 95° C. for 5 minutes. Then, real-time PCR (second reaction) was performed by repeating denaturation at 95° C. for 10 seconds, annealing with the primer and the CataCleave™ probe and reaction with RNase HII at 55° C. for 10 seconds, and elongation at 72° C. for 30 seconds 50 times. The first and second reactions were performed as a one-step reaction in the same tube using Roche Lightcycler 480. In addition, PCR amplification was observed in real-time using the LightCycler 480 Software v1.5.0.

Example 3

Detection of HIV-2 Using CataCleave™ Probe

Total RNA of HIV-2 that is used as a template in real-time PCR was subjected to extraction using Trizol reagent (Invitrogen).

Real-time PCR of HIV-2 NIHZ was performed using a various combinations of a forward primer of AF14 (SEQ ID NO: 1), AF15 (SEQ ID NO: 2), or AF16 (SEQ ID NO: 3), a reverse primer of DR13 (SEQ ID NO: 6), DR14 (SEQ ID NO: 7), DR15 (SEQ ID NO: 8), or DR24 (SEQ ID NO: 9), and a CataCleave™ probe (HIV2-P2 (SEQ ID NO: 10)). FIG. 1 shows amplification curves of the real-time PCR. In FIG. 1, the combination of AF14/DR24 is in closed circles, AF15/DR13 is in open circles, AF15/DR14 is in closed triangles, AF15/DR15 is in open triangles, AF15/DR24 is in closed squares, and AF16/DR15 is in open squares. Table 2 below shows $C_t$ values (the numbers of cycles when the amount of the PCR products increased to a predetermined level) based on the amplification curves of FIG. 1. In the experiment, the initial number of copies of the template was 5.0E+06.

The results shown below indicate that amplification could be performed with 5 copies in cases when primer sets of AF14/DR24 and AF15/DR24 were used, when the real-time PCR was performed using the primer set and CataCleave™ probes. Meanwhile, fluorescence was not detected in a control to which distilled water was added instead of the RNA template.

TABLE 2

| No. of copies of template | AF14/ DR24 | AF15/ DR13 | AF15/ DR14 | AF15/ DR15 | AF15/ DR24 | AF16/ DR15 |
|---|---|---|---|---|---|---|
| Distilled Water | N | N | N | N | N | N |
| 5 | 37.71 | N | N | N | 36.66 | N |
| 50 | 34.87 | 35.64 | 35.85 | 35.73 | 36.29 | 35.93 |
| 500 | 31.69 | 32.14 | 31.60 | 31.85 | 31.78 | 31.95 |
| 5,000 | 28.51 | 28.33 | 28.18 | 28.31 | 28.18 | 28.57 |
| 50,000 | 24.98 | 24.98 | 24.83 | 24.92 | 24.84 | 25.22 |
| 500,000 | 21.59 | 21.48 | 21.29 | 21.47 | 21.53 | 21.75 |
| 5,000,000 | 18.15 | 17.97 | 17.85 | 17.90 | 17.93 | 18.15 |

Example 4

Method of Detecting HIV-2 Using Real-Time PCR

Real-time PCR of HIV-2 NIHZ was performed using a forward primer of BF2 (SEQ ID NO: 4), a second forward primer of BF2B (SEQ ID NO: 5), a reverse primer of DR15 (SEQ ID NO: 8), and a CataCleave™ probe (HIV2-P2 (SEQ ID NO: 10)). FIG. 2 shows amplification curves of the real-time PCR. In FIG. 2, the combination of BF2/BF2B/DR15 is in closed circles. Table 3 below shows $C_t$ values (the numbers of cycles when the amount of the PCR products increased to a predetermined level) based on the amplification curves of FIG. 2. In the experiment, the initial number of copies of the template was 10,000,000. The results shown below indicate that amplification could be performed with 10 copies of HIV-2 template RNA when the real-time PCR was performed using the BF2/BF2B/DR15 primer set and HIV2-P2 Cata-Cleave™ probe. Meanwhile, fluorescence was not detected in a control to which distilled water was added instead of the RNA template.

TABLE 3

| No. of copies of template | BF2/BF2B/DR15 |
|---|---|
| Distilled Water | N |
| 10 | 37.88 |
| 100 | 34.96 |
| 1000 | 31.16 |
| 10,000 | 27.76 |
| 100,000 | 24.22 |
| 1,000,000 | 20.71 |
| 10,000,000 | 17.11 |

According to the results, HIV-2 strains can be efficiently detected with a reduced amount of samples using the primer sets and CataCleave™ probes, and thus time and effort for detecting HIV-2 strains are reduced.

Example 5

Method of Detecting HIV-2 Using Real-Time PCR

Figure 3:
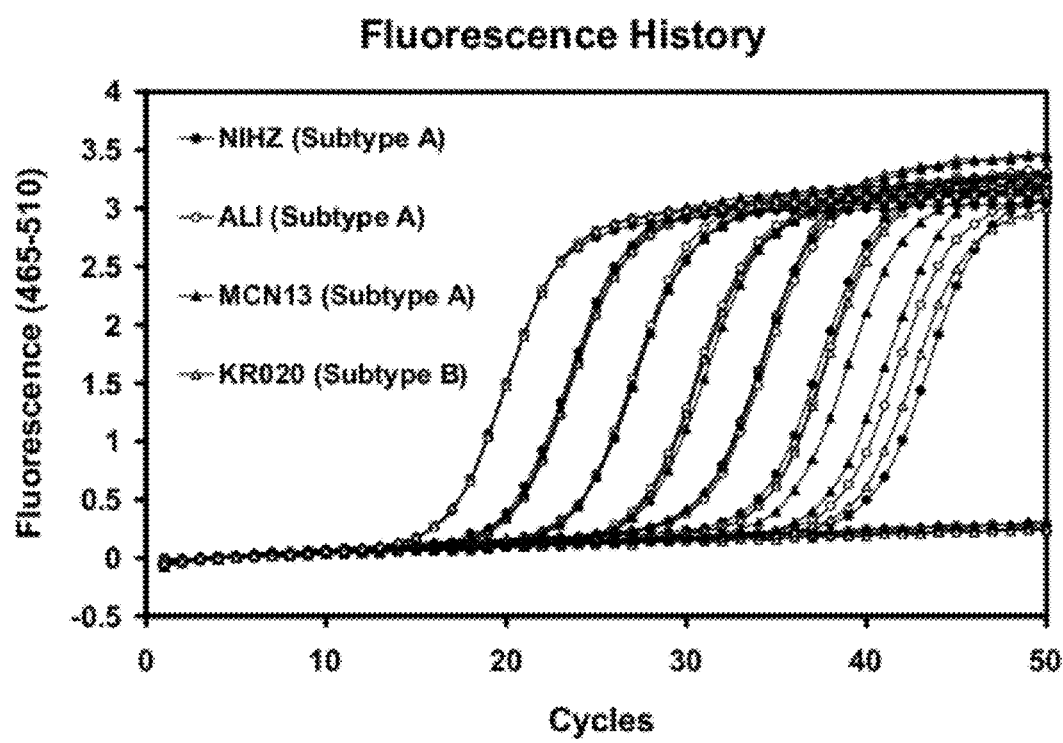
FIG. 3 shows amplification curves obtained by real-time polymerase chain reaction (PCR) of HIV-2 NIHZ using a kit according to an embodiment of the present invention.

Real-time PCR of HIV-2 NIHZ was performed using a forward primer of BF2 (SEQ ID NO: 4), a second forward primer of BF2B (SEQ ID NO: 5), a reverse primer of DR15 (SEQ ID NO: 8), and a CataCleave™ probe (HIV2-P2 (SEQ ID NO: 10)). FIG. 3 shows amplification curves of the real-time PCR. In FIG. 3, the combination of BF2/BF2B/DR15 is in closed circles. Table 4 below shows $C_t$ values (the numbers of cycles when the amount of the PCR products increased to a predetermined level) based on the amplification curves of FIG. 3. In the experiment, the initial number of copies of the template was 10,000,000. The results shown below indicate that amplification could be performed with 10 copies of HIV-2 template RNA when the real-time PCR was performed using the BF2/BF2B/DR15 primer set and HIV2-P2 Cata-Cleave™ probe. Meanwhile, fluorescence was not detected in a control to which distilled water was added instead of the RNA template.

TABLE 4

| No. of copies of template Distilled Water | NIHZ (Subtype A) | ALI (Subtype A) | MCN13 (Subtype A) | KR020 (Subtype B) |
|---|---|---|---|---|
| 10 | 40.15 | 38.33 |  | 39.28 |
| 100 | 34.10 | 34.48 | 37.72 | 34.48 |
| 1000 | 30.77 | 31.05 | 35.60 | 30.91 |
| 10,000 | 27.29 | 27.23 | 30.99 | 27.24 |
| 100,000 | 23.79 | 23.80 | 27.71 | 23.79 |
| 1,000,000 | 20.03 | 20.18 | 23.77 | 20.25 |
| 10,000,000 | 16.59 | 16.68 | 20.19 | 16.71 |

According to the results, HIV-2 strains can be efficiently detected with a reduced amount of samples using the primer sets and CataCleave™ probes, and thus time and effort for detecting HIV-2 strains are reduced.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A kit for detecting HIV-2 strains, said kit comprising a pair of primers and a probe selected from the group consisting of the following primer sets and probes:
- a primer set comprising a primer having the nucleotide sequence of SEQ ID NO: 1 and a primer having the nucleotide sequence of SEQ ID NO: 9 and a probe having the nucleotide sequence of SEQ ID NO: 10;
- a primer set comprising a primer having the nucleotide sequence of SEQ ID NO: 2 and a primer having the nucleotide sequence of ID NO: 6 and a probe having the nucleotide sequence of SEQ ID NO: 10;
- a primer set comprising a primer having the nucleotide sequence of SEQ ID NO: 2 and a primer having the nucleotide sequence of SEQ ID NO: 7 and a probe having the nucleotide sequence of SEQ ID NO: 10;
- a primer set comprising a primer having the nucleotide sequence of SEQ ID NO: 2 and a primer having the nucleotide sequence of SEQ ID NO: 8 and a probe having the nucleotide sequence of SEQ ID NO: 10;
- a primer set comprising a primer having the nucleotide sequence of SEQ ID NO: 2 and a primer having the nucleotide sequence of SEQ ID NO: 9 and a probe having the nucleotide sequence of SEQ ID NO: 10;
- a primer set comprising a primer having the nucleotide sequence of SEQ ID NO: 3 and a primer having the nucleotide sequence of SEQ ID NO: 8 and a probe having the nucleotide sequence of SEQ ID NO: 10;
- a primer set comprising a primer having the nucleotide sequence of SEQ ID NO: 4 and a primer having the nucleotide sequence of SEQ ID NO: 8 and a probe having the nucleotide sequence of SEQ ID NO: 10
- a primer set comprising a primer having the nucleotide sequence of SEQ ID NO: 5 and a primer having the nucleotide sequence of SEQ ID NO: 8 and a probe having the nucleotide sequence of SEQ ID NO: 10, and
- a primer set comprising a first primer having the nucleotide sequence of SEQ ID NO: 4, a second primer having the nucleotide sequence of SEQ ID NO: 5, and a third primer having the nucleotide sequence of SEQ ID NO: 8 and a probe having the nucleotide sequence of SEQ ID NO: 10.

2. The kit of claim 1, which further comprises an amplifying polymerase activity and an RNase H activity.

3. The kit of claim 1, which further comprises a reverse transcriptase activity.

4. The kit of claim 1, wherein a 5' end of each probe is labeled with a fluorescence label, or a 3' end of each of the probes is labeled with a fluorescence quencher.

5. The kit of claim 1, further comprising a mixture comprising dATP, dCTP, dGTP, and dTTP; a DNA polymerase; RNase HII; and a buffer solution.

6. The kit of claim 1, further comprising uracil-N-glycosylase.

7. The kit of claim 1, wherein the probe is linked to a solid support.

8. The kit of claim 1, wherein the probe is present as a free form in a solution.

9. The kit of claim 2, wherein the amplifying polymerase activity is the activity of a thermostable DNA polymerase.

10. The kit of claim 2, wherein the RNAse H activity is the activity of a thermostable RNAse H.

11. The kit of claim 2, wherein the RNAse H activity is a hot start RNAse H activity.

* * * * *

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Forward Primer (AF14)

<400> SEQUENCE: 1
gccaaggagt agtagaagca atgaatcacc                                        30

<210> SEQ ID NO 2
<211> LENGTH: 31
<212> TYPE: DNA
<213> ORGANISM: Artificial Sequence
<220> FEATURE:
<223> OTHER INFORMATION: Forward Primer (AF15)

<400> SEQUENCE: 2
gccaaggagt agtagaagca atgaatcacc a                                      31

<210> SEQ ID NO 3
<211> LENGTH: 30
<212> TYPE: DNA
<213> ORGANISM: Artificial Sequence
<220> FEATURE:
<223> OTHER INFORMATION: Forward Primer (AF16)

<400> SEQUENCE: 3
ccaaggagta gtagaagcaa tgaatcacca                                        30

<210> SEQ ID NO 4
<211> LENGTH: 30
<212> TYPE: DNA
<213> ORGANISM: Artificial Sequence
<220> FEATURE:
<223> OTHER INFORMATION: Forward Primer (BF2)

<400> SEQUENCE: 4
tagtactaat ggcagttcat tgcatgaatt                                        30

<210> SEQ ID NO 5
<211> LENGTH: 30
<212> TYPE: DNA

```
<213> ORGANISM: Artificial Sequence
<220> FEATURE:
<223> OTHER INFORMATION: Forward Primer (BF2B)

<400> SEQUENCE: 5
ttgtactaat ggcagctcac tgcatgaatt                                    30

<210> SEQ ID NO 6
<211> LENGTH: 30
<212> TYPE: DNA
<213> ORGANISM: Artificial Sequence
<220> FEATURE:
<223> OTHER INFORMATION: Reverse Primer (DR13)

<400> SEQUENCE: 6
acagctgatc tctgccttct ctgaaataga                                    30

<210> SEQ ID NO 7
<211> LENGTH: 30
<212> TYPE: DNA
<213> ORGANISM: Artificial Sequence
<220> FEATURE:
<223> OTHER INFORMATION: Reverse Primer (DR14)

<400> SEQUENCE: 7
cagctgatct ctgccttctc tgaaatagac                                    30

<210> SEQ ID NO 8
<211> LENGTH: 30
<212> TYPE: DNA
<213> ORGANISM: Artificial Sequence
<220> FEATURE:
<223> OTHER INFORMATION: Reverse Primer (DR15)

<400> SEQUENCE: 8
agctgatctc tgccttctct gaaatagacc                                    30

<210> SEQ ID NO 9
<211> LENGTH: 30
<212> TYPE: DNA
<213> ORGANISM: Artificial Sequence
<220> FEATURE:
<223> OTHER INFORMATION: Reverse Primer (DR24)

<400> SEQUENCE: 9
ctgccttctc tgaaatagac ccgaaaattt                                    30

<210> SEQ ID NO 10
<211> LENGTH: 24
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (7)..(10)
<223> OTHER INFORMATION: RNA Region
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (23)..(23)
<223> OTHER INFORMATION: n is inosine

<400> SEQUENCE: 10
ttaaaagaag gngaggaata ggng                                          24
```

```
<210> SEQ ID NO 11
<211> LENGTH: 31
<212> TYPE: DNA
<213> ORGANISM: Artificial Sequence
<220> FEATURE:
<223> OTHER INFORMATION: Synthetic Forward Primer Construct
<220> FEATURE:
<221> NAME/KEY: misc_feature
<222> LOCATION: (1)..(1)
<223> OTHER INFORMATION: absence or G
<220> FEATURE:
<221> NAME/KEY: misc_feature
<222> LOCATION: (31)..(31)
<223> OTHER INFORMATION: absence or A

<400> SEQUENCE: 11
nccaaggagt agtagaagca atgaatcacc n                             31

<210> SEQ ID NO 12
<211> LENGTH: 30
<212> TYPE: DNA
<213> ORGANISM: Artificial Sequence
<220> FEATURE:
<223> OTHER INFORMATION: Synthetic Forward Primer Construct
<220> FEATURE:
<221> NAME/KEY: misc_feature
<222> LOCATION: (2)..(2)
<223> OTHER INFORMATION: A or T
<220> FEATURE:
<221> NAME/KEY: misc_feature
<222> LOCATION: (16)..(16)
<223> OTHER INFORMATION: C or T
<220> FEATURE:
<221> NAME/KEY: misc_feature
<222> LOCATION: (20)..(20)
<223> OTHER INFORMATION: C or T

<400> SEQUENCE: 12
tngtactaat ggcagntcan tgcatgaatt                               30

<210> SEQ ID NO 13
<211> LENGTH: 41
<212> TYPE: DNA
<213> ORGANISM: Artificial Sequence
<220> FEATURE:
<223> OTHER INFORMATION: Synthetic Reverse Primer Construct
<220> FEATURE:
<221> NAME/KEY: misc_feature
<222> LOCATION: (1)..(1)
<223> OTHER INFORMATION: absence or A
<220> FEATURE:
<221> NAME/KEY: misc_feature
<222> LOCATION: (2)..(2)
<223> OTHER INFORMATION: absence or C
<220> FEATURE:
<221> NAME/KEY: misc_feature
<222> LOCATION: (3)..(3)
<223> OTHER INFORMATION: absence or A
<220> FEATURE:
<221> NAME/KEY: misc_feature
<222> LOCATION: (4)..(4)
<223> OTHER INFORMATION: absence or G
<220> FEATURE:
<221> NAME/KEY: misc_feature
<222> LOCATION: (5)..(5)
<223> OTHER INFORMATION: absence or C
<220> FEATURE:
<221> NAME/KEY: misc_feature
<222> LOCATION: (6)..(6)
<223> OTHER INFORMATION: absence or T
<220> FEATURE:
<221> NAME/KEY: misc_feature
<222> LOCATION: (7)..(7)
```

```
<223> OTHER INFORMATION: absence or G
<220> FEATURE:
<221> NAME/KEY: misc_feature
<222> LOCATION: (8)..(8)
<223> OTHER INFORMATION: absence or A
<220> FEATURE:
<221> NAME/KEY: misc_feature
<222> LOCATION: (9)..(9)
<223> OTHER INFORMATION: absence or T
<220> FEATURE:
<221> NAME/KEY: misc_feature
<222> LOCATION: (10)..(10)
<223> OTHER INFORMATION: absence or C
<220> FEATURE:
<221> NAME/KEY: misc_feature
<222> LOCATION: (11)..(11)
<223> OTHER INFORMATION: absence or T
<220> FEATURE:
<221> NAME/KEY: misc_feature
<222> LOCATION: (30)..(30)
<223> OTHER INFORMATION: absence or A
<220> FEATURE:
<221> NAME/KEY: misc_feature
<222> LOCATION: (31)..(31)
<223> OTHER INFORMATION: absence or C
<220> FEATURE:
<221> NAME/KEY: misc_feature
<222> LOCATION: (32)..(32)
<223> OTHER INFORMATION: absence or C
<220> FEATURE:
<221> NAME/KEY: misc_feature
<222> LOCATION: (33)..(33)
<223> OTHER INFORMATION: absence or C
<220> FEATURE:
<221> NAME/KEY: misc_feature
<222> LOCATION: (34)..(34)
<223> OTHER INFORMATION: absence or G
<220> FEATURE:
<221> NAME/KEY: misc_feature
<222> LOCATION: (35)..(35)
<223> OTHER INFORMATION: absence or A
<220> FEATURE:
<221> NAME/KEY: misc_feature
<222> LOCATION: (36)..(36)
<223> OTHER INFORMATION: absence or A
<220> FEATURE:
<221> NAME/KEY: misc_feature
<222> LOCATION: (37)..(37)
<223> OTHER INFORMATION: absence or A
<220> FEATURE:
<221> NAME/KEY: misc_feature
<222> LOCATION: (38)..(38)
<223> OTHER INFORMATION: absence or A
<220> FEATURE:
<221> NAME/KEY: misc_feature
<222> LOCATION: (39)..(39)
<223> OTHER INFORMATION: absence or T
<220> FEATURE:
<221> NAME/KEY: misc_feature
<222> LOCATION: (40)..(40)
<223> OTHER INFORMATION: absence or T
<220> FEATURE:
<221> NAME/KEY: misc_feature
<222> LOCATION: (41)..(41)
<223> OTHER INFORMATION: absence or T

<400> SEQUENCE: 13
nnnnnnnnnn nctgccttct ctgaaatagn nnnnnnnnnn n                41
```